United States Patent
Mulvaney, III et al.

[11] Patent Number: 6,159,358
[45] Date of Patent: Dec. 12, 2000

[54] PROCESS AND APPARATUS USING PLATE ARRANGEMENT FOR REACTANT HEATING AND PREHEATING

[75] Inventors: Robert C. Mulvaney, III, Arlington Heights; Hemant W. Dandekar, Roselle, both of Ill.

[73] Assignee: UOP LLC, Des Plaines, Ill.

[21] Appl. No.: 09/149,401

[22] Filed: Sep. 8, 1998

[51] Int. Cl.[7] .......................... C07C 5/333; C10G 35/04; B01J 8/02; F28D 7/00
[52] U.S. Cl. .......................... 208/46; 208/134; 208/146; 585/654; 585/660; 585/661; 585/662; 585/911; 585/921; 422/198; 422/200; 422/211
[58] Field of Search ........................... 208/46, 134, 146; 585/654, 660, 661, 662, 921, 911; 422/198, 200, 211

[56] References Cited

U.S. PATENT DOCUMENTS

| | | | |
|---|---|---|---|
| 4,119,526 | 10/1978 | Peters et al. | 208/64 |
| 4,126,750 | 11/1978 | Poe et al. | 568/804 |
| 4,127,389 | 11/1978 | Hackemesser et al. | 422/201 |
| 4,409,095 | 10/1983 | Peters | 208/134 |
| 4,440,626 | 4/1984 | Winter et al. | 208/65 |
| 4,677,237 | 6/1987 | Imai et al. | 585/444 |
| 4,714,593 | 12/1987 | Naito et al. | 422/197 |
| 4,750,986 | 6/1988 | Pinto | 208/64 |
| 4,810,472 | 3/1989 | Andrew et al. | 422/197 |
| 4,822,521 | 4/1989 | Fuderer | 252/376 |
| 4,880,764 | 11/1989 | Imai et al. | 502/326 |
| 4,985,231 | 1/1991 | Lywood | 423/652 |
| 5,087,792 | 2/1992 | Cottrell et al. | 585/661 |
| 5,130,106 | 7/1992 | Koves et al. | 422/216 |
| 5,300,275 | 4/1994 | Lywood | 423/655 |
| 5,405,586 | 4/1995 | Koves | 422/218 |
| 5,525,311 | 6/1996 | Girod et al. | 422/200 |

*Primary Examiner*—Walter D. Griffin
*Attorney, Agent, or Firm*—John G. Tolomei; James C. Paschall

[57] ABSTRACT

A process and apparatus produces reaction products by indirectly preheating and heating reactants by indirect heat exchange. The use of the preheating step simplifies the reaction zone design by eliminating the need for external exchangers and is particularly suited for an arrangement of plates that defines narrow channels for indirect heat exchange. The narrow channels are preferably defined by corrugated plates. The primary reaction channels will contain a catalyst for the promotion of the desired reaction product from the principal reactants. The heating fluid passes through adjacent heating channels defined by shared partition plates to provide indirect heating. At least a portion of the heating channels exchange heat with a non-catalytic portion of the reaction channels to preheat the reactants ahead of a catalytic section of the reaction channels. Catalytic combustion within the heating channels may provide in-situ heat input for the heating medium. Suitable catalysts for the heating channels may comprise oxidation promoting catalysts.

18 Claims, 7 Drawing Sheets

6,159,358

PROCESS AND APPARATUS USING PLATE ARRANGEMENT FOR REACTANT HEATING AND PREHEATING

FIELD OF THE INVENTION

This invention relates generally to plate type exchangers for indirect heat exchange and the heating of reactants to control temperature conditions in a reaction process.

BACKGROUND OF THE INVENTION

In many industries, like the petrochemical and chemical industries, contact of reaction fluids with a catalyst in a reactor under suitable temperature and pressure conditions effects a reaction between the components of one or more reactant in the fluids. Most of these reactions generate or absorb heat to various extents and are, therefore, exothermic or endothermic. The heating or chilling effects associated with exothermic or endothermic reactions can positively or negatively affect the operation of the reaction zone. The negative effects can include among other things: poor product production, deactivation of the catalyst, production of unwanted by-products and, in extreme cases, damage to the reaction vessel and associated piping. More typically, the undesired effects associated with temperature changes will reduce the selectivity or yield of products from the reaction zone.

Many arrangements seek to overcome the negative effects of endothermic chilling by supplying heat to the reaction. More traditional methods employ multiple stages of heating between adiabatic reaction stages. Other methods use in-situ heating via simultaneous reactions or indirect heat exchange to maintain an isothermal or other temperature profile within the reaction zone. U.S. Pat. No. 5,525,311 provides an example of indirect heat exchange with a heat exchange fluid to control the temperature profile within a reaction zone.

A variety of processes can employ indirect heat exchange with a reaction zone to control temperature profiles within the reaction zone. Common examples of hydrocarbon conversion reactions include: the aromatization of hydrocarbons, the reforming of hydrocarbons, the dehydrogenation of hydrocarbons, and the alkylation of hydrocarbons.

Briefly, in the catalytic reforming of naphtha, a feedstock is admixed with a recycle stream comprising hydrogen and contacted with catalyst in a reaction zone. Naphtha reforming may be defined as the total effect produced by dehydrogenation of cyclohexanes and dehydroisomerization of alkylcyclopentanes to yield aromatics, dehydrogenation of paraffins to yield olefms, dehydrocyclization of paraffins and olefms to yield aromatics, isomerization of n-paraffins, isomerization of alkylcycloparaffins to yield cyclohexanes, isomerization of substituted aromatics, and hydrocracking of paraffins. A catalytic reforming reaction is normally effected in the presence of catalyst particles comprised of one or more Group VIII noble metals (e.g., platinum, iridium, rhodium, palladium) and a halogen combined with a porous carrier, such as a refractory inorganic oxide. The halogen is normally chlorine, and alumina is a commonly used carrier. Further information on reforming processes may be found in, for example, U.S. Pat. No. 4,119,526 (Peters et al.); U.S. Pat. No. 4,409,095 (Peters); and U.S. Pat. No. 4,440,626 (Winter et al); the contents of which are herein incorporated by reference.

Catalytic dehydrogenation is another example of an endothermic process. In catalytic dehydrogenation, a feedstock is admixed with a recycle stream comprising hydrogen and contacted with catalyst in a reaction zone. Feedstocks for catalytic dehydrogenation are typically petroleum fractions comprising aromatic of paraffinic hydrocarbons. The dehydrogenation of ethyl benzene to produce styrene is well known. Paraffinic feedstocks ordinarily have from about 3 to about 18 carbon atoms. Particular feedstocks will usually contain light or heavy paraffins. A catalytic dehydrogenation reaction is normally effected in the presence of catalyst particles comprised of one or more Group VIII noble metals (e.g., platinum, iridium, rhodium, palladium) combined with a porous carrier such as a refractory inorganic oxide. Alumina is a commonly used carrier. Dehydrogenation conditions include a temperature of from about 400° to about 900° C., a pressure of from about 0.01 to 10 atmospheres, and a liquid hourly space velocity (LHSV) of from about 0.1 to 100 $hr^{-1}$. Generally the lower the molecular weight of the feed the higher the temperature required for comparable conversions. The pressure in the dehydrogenation zone is maintained as low as practicable, consistent with equipment limitations, to maximize the chemical equilibrium advantages. The preferred dehydrogenation conditions of the process of this invention include a temperature of from about 400°–700° C. and a pressure from about 0.1 to 5 atmospheres.

The effluent stream from the dehydrogenation zone generally will contain unconverted dehydrogenatable hydrocarbons, hydrogen, and the products of dehydrogenation reactions. This effluent stream is typically cooled and passed to a hydrogen separation zone to separate a hydrogen-rich vapor phase from a hydrocarbon-rich liquid phase. Generally, the hydrocarbon-rich liquid phase is further separated by means of either a suitable selective adsorbent, a selective solvent, a selective reaction or reactions or by means of a suitable fractionation scheme. Unconverted dehydrogenatable hydrocarbons are recovered and may be recycled to the dehydrogenation zone. Products of the dehydrogenation reactions are recovered as final products or as intermediate products in the preparation of other compounds. Additional information related to the operation of dehydrogenation catalysts, operating conditions, and process arrangements can be found in U.S. Pat. Nos. 4,677,237; 4,880,764 and 5,087,792; the contents of which are hereby incorporated by reference.

Other examples are processes for the production of hydrogen and carbon oxides by reforming methane in the presence of steam or carbon oxides. The steam reforming process is particularly well known and involves passage of a mixture of feedstock and steam over a steam reforming catalyst. Typical steam reforming catalyst comprises nickel and may include cobalt on refractory supports such as alpha alumina or calcium aluminate. The strong endothermic nature of the primary steam reforming reaction requires a supply of heat to maintain the reaction. Those skilled in the art routinely balance the endothermic heat requirements of the primary reforming with a partial oxidation of hydrocarbons to provide a secondary reforming reaction that supplies heat for the primary reforming stage and generates additional synthesis gas. Extensive and highly developed teachings detail methods of indirectly exchanging heat between primary and secondary reforming. The operation of an adiabatic reformer for synthesis gas production is shown in U.S. Pat. No. 4,985,231. U.S. Pat. No. 5,300,275 sets forth another basic arrangement that uses a secondary reforming reaction to supply hot gas for heating the primary reforming reaction. U.S. Pat. Nos. 4,810,472; 4,750,986; and 4,822,521 disclose particular arrangements of heat exchange reactors that indirectly exchange heat between hot gases from the secondary reforming stage and the primary reforming stage. U.S. Pat. No. 4,127,389 shows a variety of tube chamber designs for supplying heat to a primary reforming reaction from a secondary reforming reaction zone. As established by the above referenced patents, the art currently relies exclusively on tube arrangements, and most commonly, the art relies on double walled tubes referred to as "bayonet tubes" for exchanging heat between the primary and secondary reforming zones. The geometry of tubular reactors poses layout constraints that require large reactors and vast tube surface to achieve the desired high heat transfer efficiencies.

Other process applications accomplish indirect heat exchange with thin plates that define channels. The channels alternately retain catalyst and reactants in one set of channels and a heat transfer fluid in adjacent channels for indirectly heating or cooling the reactants and catalysts. Heat exchange plates in these indirect heat exchange reactors can be flat or curved and may have surface variations such as corrugations to increase heat transfer between the heat transfer fluids and the reactants and catalysts. Many hydrocarbon conversion processes will operate more advantageously by maintaining a temperature profile that differs from that created by the heat of reaction. In many reactions, the most beneficial temperature profile will be obtained by maintaining substantially isothermal conditions. In some cases, a temperature profile directionally opposite to the temperature changes associated with the heat of reaction will provide the most beneficial conditions. For such reasons it is generally known to contact reactants with a heat exchange medium in cross flow, cocurrent flow, or countercurrent flow arrangements. A specific arrangement for heat transfer and reactant channels that offers more complete temperature control can again be found in U.S. Pat. No. 5,525,311; the contents of which are hereby incorporated by reference. Other useful plate arrangements for indirect heat transfer are disclosed in U.S. Pat. No. 5,130,106 and U.S. Pat. No. 5,405,586.

Although it is known from patents such as U.S. Pat. No. 4,714,593 to directly combust fuel for the indirect heating of a reaction zone, feed preheat is still normally provided outside of the reaction zone. Typical process arrangements that provide in situ heating to control temperatures also employ some form of charge heater. The charge heater brings the entering feed to initial reaction temperature before it enters the reaction zone. The charge heater adds cost and complexity to the system.

It is, therefore, an object of this invention to improve the efficiency of heating reactants in a process that uses in-situ indirect heat exchange.

It is a further object of this invention to reduce equipment requirements in the heating of reactants.

BRIEF SUMMARY OF THE INVENTION

It has now been discovered that a modification to the method and apparatus for indirectly heating reactants in the reaction zone can eliminate the need for a charge heater. A process that employs a plurality of plates defining narrow channels for heating reactants in a catalyst containing reaction zone can extend the channels to include an upstream section that preheats the feed. The upstream preheat section contains no catalyst. The preheat zone raises the temperature of the reactants to the desired initial reaction temperature before contacting the feed with the catalyst in the reaction section of the channels. The fluid for heating the reaction section may be any heat transfer fluid that enters the heating channels at suitable conditions to provide the necessary temperature and heat to both the preheat and catalytic portions of the reaction channels. Conversely, the heat exchange fluid may be a fuel stream that undergoes combustion within the heating channels. Methane provides a particularly useful heating fluid. In some cases the heating fluid can comprise the feed or the reactant components from the reaction channels. Overall the invention conserves heat by eliminating the need for a separate heater in the process and by removing the heat losses associated therewith. In this manner the invention accomplishes a highly efficient utilization of the plate and channel reaction and heating configuration.

The presence of narrow heating channels for containing reaction and heating functions constitutes an essential requirement of this invention. The heating and reaction channels may take on a many different configurations that suit the particular process and heating fluid. The preheat portion of the reaction channel may comprise a portion along a continuous length of channel or a separate length of channel may provide the preheat portion and deliver the heated reactants to an independent reaction channel. In vertically extending channels, short loading of catalyst in the reaction channels can provide a space above or below the primary reforming section in which to preheat feed.

The heating channels and reaction channels may pass fluids in cross, cocurrent, or countercurrent flow. Countercurrent flow will provide the greatest heat input into the reaction portion of the reaction channels, and cocurrent flow will maximize heating in the preheat portion of the reaction channels.

The heating channels may contain combustion promoting catalyst for accelerating the combustion of the fuel. Where fuel is combusted in the heating channels, the combustion catalyst loading may be varied in the heating channels to accommodate the heating requirements of the feedstream and the reaction zone. Controlling the combustion rate of a fuel using catalyst in channels that indirectly heat a reaction zone by heat exchange across a heat exchange surface can moderate temperatures thereby improving conversion, selectivity or both. Temperature moderation by varying the combustion rate of the fuel can also reduce catalyst deactivation in the reaction zone. A number of different methods may vary the rate at which the combustion catalyst promotes combustion of the fuel in the heating channels. The operation may vary process conditions such as residence time/space velocity. The concentration of fuel reactants may also vary by the introduction of additional fuel or diluents. Another variation method may increase the amount of catalyst present in the heating channels. Increasing or decreasing the loading of catalytically active material on a catalyst base over the length of the heating channels will vary the combustion rate. In addition to changing the catalyst through a change in metals loading, the type of catalyst may also vary over the length of the heating channels. Furthermore, the method of this invention may simply change the amount of a uniform catalyst by varying the volume of catalyst per unit of flow length along the channels. By the use of an appropriate catalyst activity profile in the heating channels a temperature profile that maximizes conversion may be imposed in the channels where the feed conversion occurs. From a mechanical standpoint the inherent increasing or decreasing sector width of a radial flow reactor provides a ready means of varying the volume of catalyst per unit flow length along the heating channels. U.S. Pat. No. 5,405,586 shows a radial flow reactor arrangement with indirect heat exchange that may be modified in accordance with this invention to include variation in combustion of a fuel.

Plate arrangements may also vary the catalyst loading in the heating channels. Plates can occupy a portion of the channels to reduce catalyst loading in only a portion of the heat exchange channels. A thick plate may extend through a portion of the heating channels and solidly displace catalyst from a portion of the heat exchange channel. Pairs of solid plates may extend over a portion of the heat exchange channels to define sub-channel void volumes. Such central sub-channels can create thin layers of catalyst at the outside of the heating channels where less combustion is desired. The use of perforated plates may provide a particularly advantageous method of altering the catalyst loading in the heating channels. The size of the perforations may block catalyst entry into a channel sub-portion defined by the perforated plates in the heating channels while still permitting gas flow therethrough. Alternately, the perforated plates may extend through the entire length of the heating channels, but with varied perforation sizes. In vertically oriented channels, small perforations in an upper portion of the plate may prevent catalyst particles from entering the upper space between the plates while larger perforations in a lower portion of the plates passes catalyst into a lower sub-channel area to increase the relative catalyst volume of catalyst per unit length of channel. Use of perforated plates in this manner can greatly facilitate loading and unloading of the combustion catalyst and even permit on-stream change-out of the varied combustion catalyst loading.

Distribution chambers along the channel paths may provide sites for intermediate injection of reactants or heating medium. Distribution chambers may be provided at the ends of channels or along the mid points, as desired. One arrangement of such manifolds uses two or more separate stacks of heat exchange plates or "reaction stacks" to conduct different reactions and heat exchange steps in isolated banks. For example, one arrangement of alternating narrow channels in a reaction stack may contain catalyst for the heating channels only while a downstream reaction stack contains catalyst in both the reaction and heating channels. A system of manifolds passes the isolated preheated feed and heating fluid effluent to another section of heating channels and reaction channels that again indirectly contact the heating fluid with the reactants. Integration of the manifolds with external pipes can further enhance process control by the intermediate addition or withdrawal of heating fluid or reactants.

Suitable plate arrangement may use relatively smooth plates with intermediate spacers placed intermittently between the plates to preserve the channel space and to introduce turbulence for promoting heat transfer. A spiral wound arrangement of narrowly spaced apart channels can provide a high degree of contacting and heat exchange. A preferred form of the heat exchange elements comprise relatively flat plates having corrugations defined therein. The corrugations serve to maintain spacing between the plates while also supporting the plates to provide a well supported system of narrow channels. Additional details on the arrangement of such plate systems are again shown in U.S. Pat. No. 5,525,311.

Suitable plate arrangements may also incorporate perforated plates. Most advantageously perforated plates would allow the controlled quantities of the reactants to flow directly from the primary reforming zone channels as feed into the secondary reforming zone channels. Perforated plates would disperse the introduction of the reactants over a desired portion of the secondary heating channels. Those skilled in the art will recognize other variations in plate configurations that can provide additional benefits to the integration of the heating and reaction channels.

Accordingly, in one embodiment this invention is a process for contacting reactants with a catalyst in a reaction zone and for indirectly heating the reactants by contact with a heating medium. The process passes a reactant stream through a plurality of narrow reaction channels defined by principal spaced apart plates and heats the reactant stream in the absence of catalyst in a first portion of the narrow reaction channels. The process also passes a heating medium through a plurality of narrow heating channels defined by the principal plates and indirectly heats the reactant stream in the first portion of the reaction channels across the plates with the heating medium in a preheat portion of the heating channels to provide a heated reactant stream in the reaction channels. The heated reactant stream passes through a second portion of the reaction channels and contacts the heated reactant stream with a catalyst in the second portion of the reaction channels to produce a reacted stream while indirectly heating the second portion of the reaction channels with heating medium as it passes through a primary heating portion of the heating channels. In a more limited form of this embodiment, methane enters the heating channels and undergoes oxidation to provide the heating fluid. Preferably, the methane contacts a combustion catalyst or oxidation catalyst in the heating channels.

In another embodiment, this invention comprises an apparatus for contacting reactants with a catalyst in a reaction zone while indirectly heating the reactants by contact with combustion gases formed in a heat producing zone. The apparatus includes a plurality of alternate reaction channels and heating channels defined by a plurality of primary plates to have a reactant inlet at one end of the reaction channels, a reactant outlet at an opposite end of the reaction channels, a heating fluid inlet at one end of the heating channels and a heating fluid outlet at the opposite end of the heating channels. The reaction channels include means for excluding a solid catalyst from a preheat portion of the reaction channels that is located downstream of the reactant inlet and for retaining a solid catalyst in a catalytic portion of the reaction channels located downstream of the preheat portion. The apparatus may include means for delivering a reactant stream to the reactant inlet and for withdrawing a reacted stream from the reactant outlet and means for delivering a heating fluid to the heating fluid inlet and withdrawing a heating fluid from the heating fluid outlet. In another form of this embodiment, the heating channels may define a combustion zone and retain a combustion promoting catalyst. Preferably, the retained catalyst comprises an oxidation catalyst and an oxygen conduit supplies oxygen to the heating channels.

The heating medium may be supplied by a separate stream, a portion of the reacted stream or a portion of the reactant stream. For example, in the case of paraffin isomerization there is often a need to saturate benzene, the benzene that routinely accompanies the paraffin feed. The heat generated by the saturation of benzene can indirectly heat the isomerization reaction zone while also preheating the feed that enters the isomerization zone. In such a process, a feedstream comprising $C_4$ to $C_6$ paraffinic hydrocarbons and typically at least 2 mol % benzene passes to a benzene saturation zone comprising saturation channels. A plurality of spaced apart plates define the saturation channels and provide a heat exchange surface. Admixing a hydrogen-containing stream with the feedstream produces a combined feed. The combined feed contacts a benzene saturation catalyst in the benzene saturation zone to saturate benzene, release heat, and produce an at least partially saturated effluent. The plurality of spaced apart plates define heat exchange channels. Indirect heat exchange across the plurality of spaced apart plates with a cooling fluid in the heat exchange channels cools the saturation reaction zone effluent. At least a portion of the at least partially saturated effluent passes to an isomerization zone as an isomerization feed that isomerizes the isomerization feed in the isomerization zone by contact with an isomerization catalyst to produce an isomerization effluent. At least one of the feedstream, combined feed, isomerization feed or isomerization zone effluent passes through the heat exchange channels as the cooling fluid. Integral heating of the incoming feed with the feed to the saturation zone reduces the temperature of the saturation zone and reduces or eliminates the need for importation of heat into the process. Reducing or eliminating the importation of heat lowers process temperatures overall to provide more favorable equilibrium conditions for both the saturation and isomerization reactions.

Additional embodiments, arrangements, and details of this invention are disclosed in the following detailed description of the invention.

DETAILED DESCRIPTION OF THE INVENTION

Figure 1:
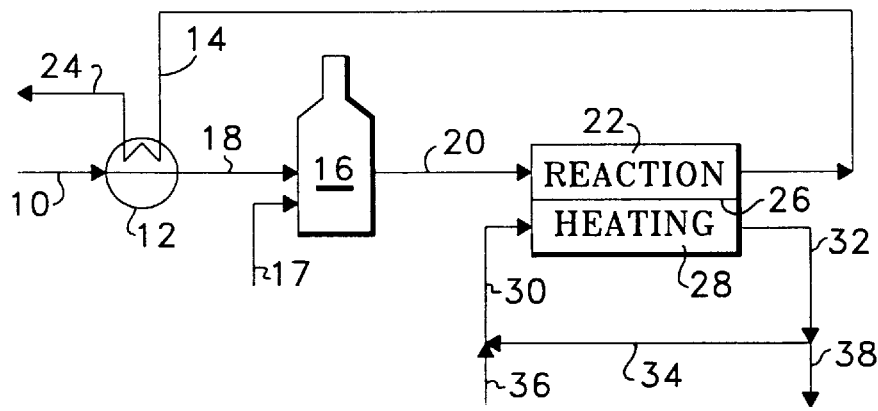
FIG. 1 is a schematic flow diagram of a reaction zone, heating zone, heat exchanger, and charge heater arrangement in accordance with the prior art.
Figure 2:
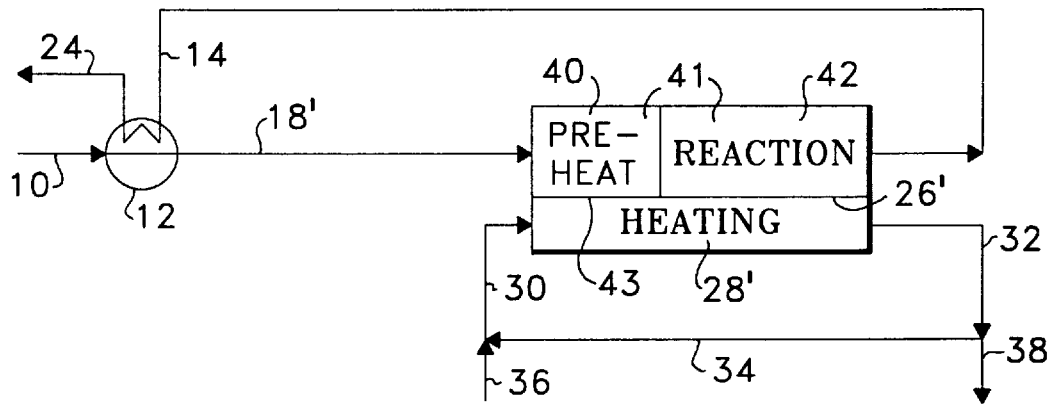
FIG. 2 is a schematic flow diagram of a reaction zone, heating zone, and heat exchanger arrangement in accordance with this invention.

FIGS. 1 and 2 compare the prior art with the instant invention. In FIG. 1 a process stream enters the process arrangement via line 10 and passes through a heat exchanger 12 which recovers heat from a reaction zone effluent stream 14. Partially heated feed from exchanger 12 passes to a charge heater 16 via a line 18. A line 17 adds fuel to the charge heater 16. A line 20 carries the heated feedstream into contact with a catalyst in a reaction zone 22 for an endothermic reaction to produce the effluent stream 14 that exits the process downstream of heat exchanger 12 via a line 24. Reaction zone 22 exchanges heat across a heat transfer plate 26 with a heating zone 28. Line 30 passes a heating medium into heating zone 28. After heat exchange in zone 28 line 32 withdraws the cooled heating medium.

In a preferred form of the invention, the heating medium comprises a fuel stream for combustion in the heating zone 28. Line 34 recirculates a portion of the heating medium back to the inlet of the heating zone via a line 34. Fresh fuel enters the heating medium loop via a line 36 while a line 38 purges spent fuel components. The heating medium may comprise methane and air or any other suitable combustible fuel. Heating zone 28 may also contain a combustion catalyst.

FIG. 2 modifies the prior art arrangement of FIG. 1 by adding a preheat zone 40 and eliminating the charge heater 16. Thus, the feedstream again enters the process through line 10 and undergoes heat exchange with the outgoing effluent stream 14 in exchanger 12. Line 18' passes the partially heated feed into preheat section 40 of reaction zone 41. Preheat section 40 does not contain catalyst and serves to heat the remainder of the feed to the desired temperature for the reaction that occurs in a catalytic reaction section 42 of reaction zone 41. After heat exchange, the product stream leaves the process through line 24. On the heating side, a heating fluid 30 again passes through the heating zone 28' and leaves the heating zone through line 32. Lines 36, 34, and 38 can again provide addition, recirculation, and purging when the heating fluid comprises a fuel stream.

Heating zone 28' heats the preheat section 40 and catalytic reaction section 42 of the reaction zone 41 across a heat exchange plate 26'. The amount of heating necessary in preheat zone 40 as well as the temperature and heat capacity of the heating fluid will determine the relative length of preheat zone 40 and the amount of surface area provided by a preheat section 43 of plate 26'. Where reactants or products from the reaction zone 41 provide fuel to the heating zone, fuel may be diverted from line 10 or 14 into the heating zone 28'. Fuel may also be directly injected from the reaction zone 41 into the heating zone across plate 26'. Sufficient pressure drop from the reaction zone to the heating zone can permit the use of a perforated plate and prevent the backflow of fluid from the heating zone to the reaction zone. Perforations sized to control the flow may be provided across the heat transfer plate in preheat portion 43, catalytic reaction section 42, or both.

This invention may be useful for any endothermic process that uses a heating medium to preheat the reactant stream to the desired reaction temperature and uses the heating medium to maintain the temperature of reactant stream after. Processes particularly suited for use by this invention are those wherein the reactant undergoes heating by combustion of a fuel. This invention may be particularly useful in autothermic processes where the conversion of a reactant or a portion of an endothermically reacted stream provides fuel for an exothermic reaction that heats the endothermic reaction. Additional requirements of this process for compatibility with a plate exchanger arrangement will typically require that there be a relatively low ΔT between the exothermic and endothermic reaction zones along with the relatively low ΔP across the plate sections. Differential temperatures of 200° C. or less are preferred for this invention. Differential pressures preferably will not exceed 0.7 MPa.

Many reactions for the production of hydrocarbon and chemical products meet these requirements. Examples of autothermic process include the production of raw ammonia synthesis gas, production of raw hydrogen streams, and the production of synthesis gas for conversion to organic compounds.

Looking specifically at the production of raw synthesis gas as an example, such process ordinarily include a primary step of reforming a hydrocarbon feedstock with steam to give a gas containing carbon oxides, hydrogen, methane, and unreacted steam. In the production of synthesis gas, a fluid hydrocarbon such as natural gas is converted to a hot reformed gas mixture containing principally hydrogen and carbon monoxide according to the reaction (1):

$$CH_4 + H_2O \leftrightarrow CO + 3H_2 \qquad (1)$$

which is generally known as primary reforming and is widely used in the production of synthesis gas or pure hydrogen. This endothermic reaction is carried out in the practice of this invention by passing a gaseous mixture of fluid hydrocarbon and steam through a preheat section of a reaction channel that is free of catalyst and then through a catalyst containing section of reaction channel. A suitable catalyst composition fills the catalytic section of the reaction channels.

The necessary heat is supplied to the reaction channels by a secondary reforming reaction that oxidizes a fluid hydrocarbon fuel. The fluid hydrocarbon fuel may comprise a side stream from the fluid hydrocarbon feedstream or a portion of the primary reforming effluent stream. The oxidation reaction supplies the heat to the primary reformer by indirect heat exchange across heat exchange plates. The following reactions occur in the heating channels that contain the secondary reforming zone:

$$2CO + O_2 \rightarrow 2CO_2, \qquad (2)$$

$$2CH_4 + O_2 \rightarrow 4H_2 + 2CO. \qquad (3)$$

and $$2H_2 + O_2 \rightarrow 2H_2O.$$

Reactions (2), (3), and (4) are exothermic reactions that tend to occur quite rapidly in the secondary reaction space. As the resulting gas mixture passes through the catalyst bed of the secondary reformer zone, the remaining methane is converted by reaction with steam in accordance with reaction (1) above and by the reaction with oxygen according to reaction (2) above so that very little methane remains in the product gas of the process. The strongly endothermic reaction (1) is a relatively slow reaction that occurs throughout the passage of the gases through the catalyst bed of the secondary reforming zone, thereby cooling the gases from the high temperatures reached by reactions (2), (3), and (4) that occur toward the feed end of the secondary reaction zone. In the practice of the invention, the proportions of oxygen and of the fluid hydrocarbon feed passed to the integrated primary-secondary reformers maintain an essentially, or completely, autothermal process with essentially no external fuel requirement. An advantageous feature of the invention is the flexibility of being able to by-pass a portion of the hydrocarbon feedstream directly to the secondary reforming reaction space at the feed end of the secondary reforming zone.

Typical operating temperatures for the production of a raw synthesis gas are in the range of from 420–950° C. The specific operating pressures employed are principally influenced by the pressure requirements of the subsequent processing operations in which the reformed gas mixture is employed. Any super atmospheric pressure can be used in the practice of most reforming operations and is suitable for most applications of the apparatus and process of this invention. Operating pressures within the process usually lie within a range of from 2 to 10 MPa. In the production of synthesis gas for ammonia production, the effluent from the primary reforming step reacts catalytically with an oxygen and nitrogen-containing mixture, typically air, to convert additional portions of methane and introduce nitrogen into the product stream. After the shift reaction and $CO_2$ removal, the raw ammonia synthesis gas will have a desirable hydrogen to nitrogen ratio of approximately 2.5 to 3.0.

The reactant stream contacts a catalyst in each of the reaction channels. Catalysts employed in steam reforming are well known. Specific examples of reforming catalysts that can e used are nickel, nickel oxide, cobalt oxide, chromia, molybdenum oxide, and rhodium based catalyst on an α-alumina support. The catalyst can be employed with promoters and receive various special treatments known in the art for enhancing its properties. Promoted nickel oxide catalysts are generally preferred, and the catalytic section of the primary reformer channels is packed with solid catalyst granules, usually comprising the catalytic agent deposited on a suitable inert carrier material. The secondary reforming zone commonly contains a bed of similar catalyst material.

As an alternate to a particulate catalyst, the catalyst may also be coated on the surface of the plates in the various reforming zones. It may be particularly advantageous to coat the primary reforming catalyst onto the plates to provide an upper catalytic section and a lower catalyst-free section that is maintained in heat exchange relationship with a catalytic secondary reforming section across the channel defining plates.

Figure 3:
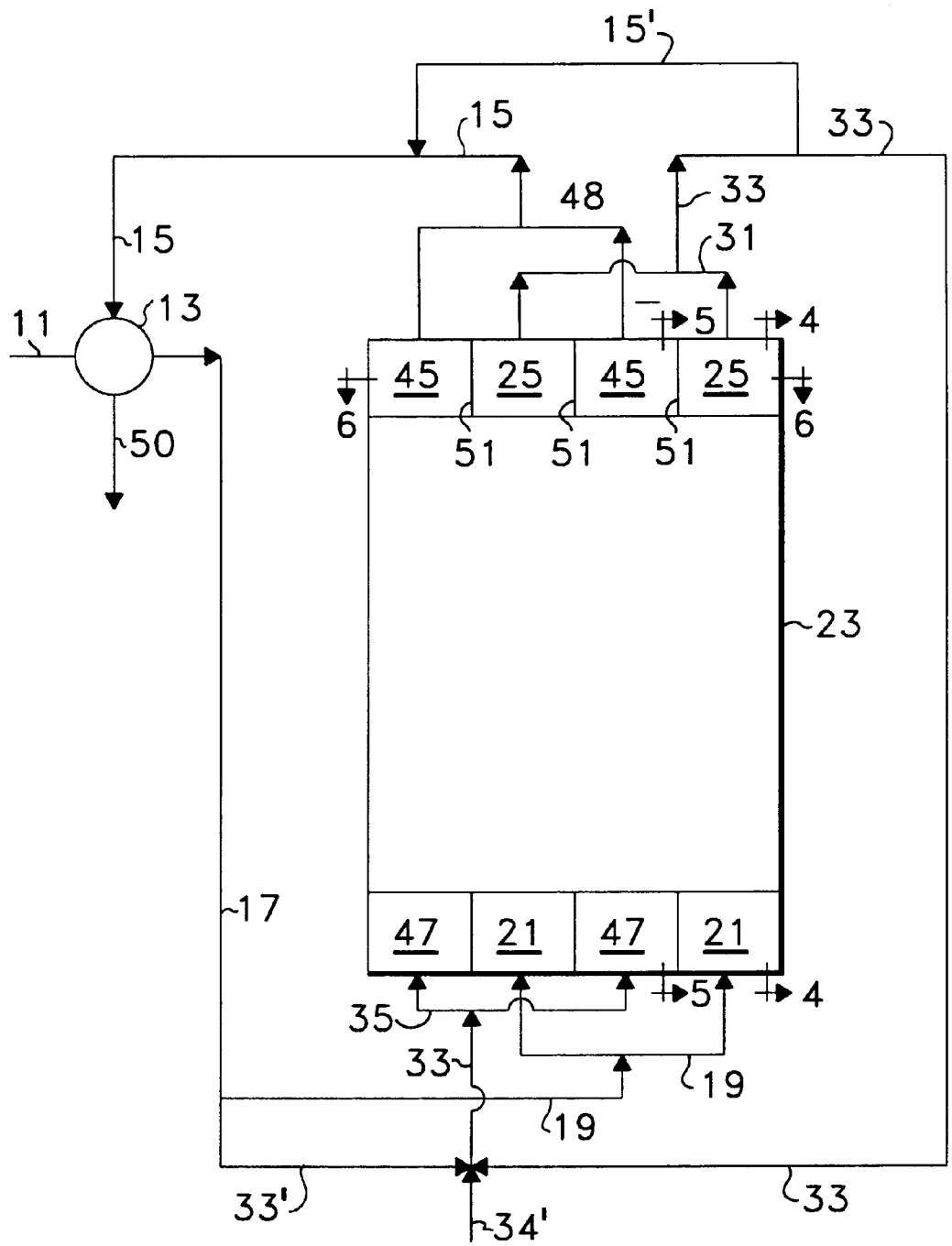
FIG. 3 is a schematic diagram of vertical plate channel exchanger incorporating an arrangement of this invention.
Figure 4:
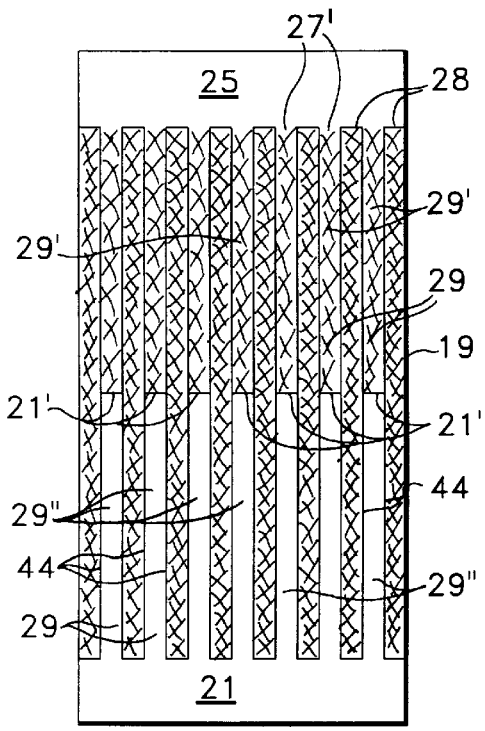
FIG. 4 is a section of the schematic heat exchange reactor shown in FIG. 3 at section 4—4.

Looking then at FIG. 3, for an alternate flow arrangement of this invention, a synthesis gas feed comprising natural gas and steam in a steam to methane proportion of from 1.5 to 4 enters the process via line 11 and undergoes heat exchange in a conventional heat exchanger 13 with a synthesis gas product stream carried by a line 15. The preheated feedstream passes via line 17 to a distribution header 19. Distribution header 19 supplies the heated feed to distribution spaces 21 in a heat exchange reactor 23. As further shown by FIG. 4, distribution space 21 distributes the heated synthesis gas to a plurality of primary reforming reaction channels 29 by plates 44. Reaction channels retain a reforming catalyst in upper portions 29' and a catalyst free preheating zone in lower portions 29". The mid-portions 21' of the reaction channels 29 are open to gas flow, but they have an appropriate screen material located thereacross to prevent catalyst from falling from upper channel portions 29'. The heated reforming reactants pass through the channels 29. Collection space 25 collects the effluent from the primary reforming zone across the open tops 27' of channels 29. As shown in FIG. 3, a manifold 31 collects the primary reforming effluent from collection spaces 25 and transfers the effluent, minus any amount taken by line 15', via a line 33 to the secondary reforming zone. Line 15' by-passes primary reforming zone effluent directly to the product of line 15.

Line 33 passes the primary effluent to a distribution manifold 35 that distributes the hot gases to distribution spaces 47. A portion of the natural gas feed may by-pass the reaction channels 29 via line 33' and directly enter the secondary reforming zone. Line 34' provides oxygen or air for combustion and may also provide additional fuel to the secondary reaction zone as required. Some initial reaction of the primary reforming effluent may take place in manifold 35 and distribution space 47. Combining $O_2$ with the feedstream or the primary reactor effluent must be done in a manner to avoid the presence of oxygen and other combustibles in general or localized proportions that fall within potential explosive ranges. Precautions may include the use of mixing elements as well as specialized header design to maintain safe proportions of the mixtures. Suitable header designs may include packing or other volume displacement material to minimize the volume of oxygen and fuel mixtures upstream of the secondary reforming reaction.

Figure 5:
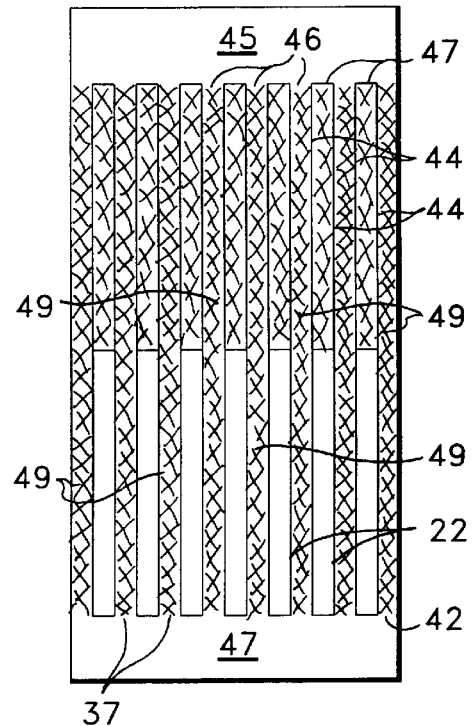
FIG. 5 is a section of the schematic heat exchange reactor shown in FIG. 3 taken at section 5—5.

As further shown by FIG. 5 which depicts section 5–5 of FIG. 3, distribution spaces 47 distribute the hot gas to inlets 37 of heating channels 49. As opposed to distribution space 21, distribution space 47 has the bottoms of reaction channels 29 closed to gas and catalyst flow to prevent the flow of secondary reforming effluent therein. The principal secondary reforming reaction will take place in contact with the catalyst contained in the heating channels. Contact with a suitable secondary reforming catalyst in the heating channels directly produces heat for indirect heating of the reactants in the primary reforming zone contained within the reaction channels. As the hot gases pass upwardly through heating channels 49, the large surface area provided by the plates 44 that define the reaction and heating channels efficiently transfer heat into the reaction channels 29.

Collection space 45 collects the cooled secondary reforming gas from the open outlets 46 of heating channels 49. As shown again in FIG. 3, a manifold 48 gathers the collected secondary reforming effluent and transfers it into product line 15 for recovery downstream of exchanger 13 via line 50.

Figure 6:
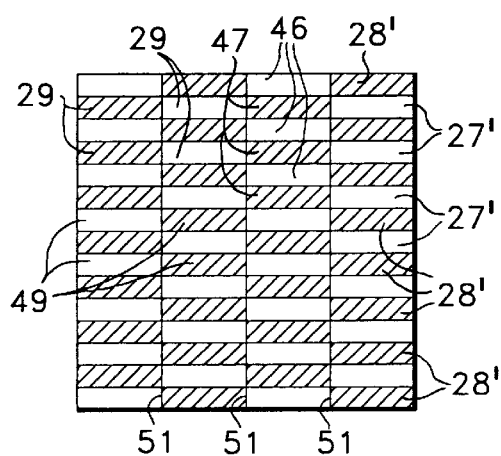
FIG. 6 is a horizontal section of the schematic heat exchange reactor shown in FIG. 3 taken at section 6—6.

The arrangement of collection spaces 25 and 45 to selectively collect the primary reforming effluent and the secondary reforming effluent is more fully appreciated from FIG. 6. As shown by FIG. 6, those portions of reaction channels 29 that coincide with collection space 25 maintain outlets 27' open for free communication therewith. Conversely, those portions of heating channels 49 that coincide with collection space 25 have a closure 28' that prevents fluid communication with collection space 25. Collection space 45 has the reverse relationship to channels 29 and 45 wherein coinciding portions of channels 49 communicate openly across outlet 46 while coinciding portions of channels 29 are blocked from communication with collection space 45 by closures 47. Distribution spaces 21 and 47 have a similar arrangement for establishing and restricting fluid communication with the desired channels. FIG. 6 also shows the partitions 51 that internally segregate collection spaces 24 from collection spaces 45.

Suitable plates for this invention will comprise any plates that allow a high heat transfer rate. Thin plates are preferred and usually have a thickness of from 1 to 2 mm. The plates are typically composed of ferrous or non-ferrous alloys such as stainless steel. Preferred alloys for the plates will withstand extreme temperatures and contain high proportions of nickel and chrome. The plates may be formed into curves or other configurations, but flat plates are generally preferred for stacking purposes. Again each plate may be smooth and additional elements such as spacers of punched tabs may provide fluid turbulence in the channels. Preferably, each plate has corrugations that are inclined to the flow of reactants and heat exchange fluid.

Figure 7:
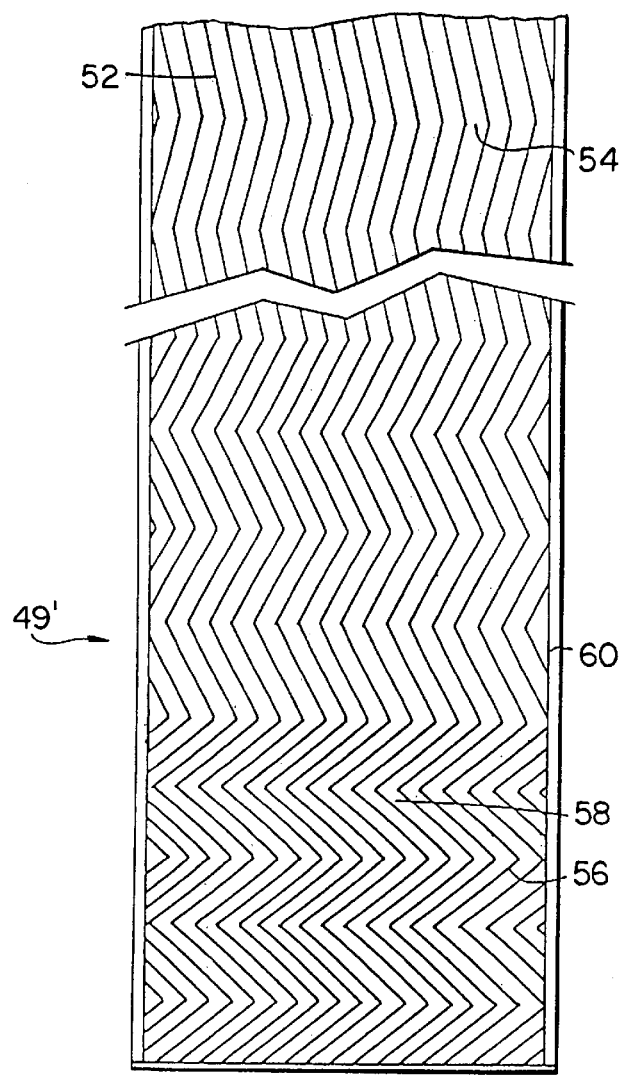
FIG. 7 is a schematic drawing of a flat plate element showing a corrugation pattern.

FIG. 7 shows the preferred corrugation arrangement where the plates 44 that divide the central portion of heat exchange reactor 23 into heating channels and reaction channels are formed by plates 49' having a corrugation arrangement as shown in FIG. 7. The corrugation pattern can serve at least two functions. In addition to structurally supporting adjacent plates, the corrugations promote turbulence for enhancing heat exchange efficiency in the narrow reaction channel. FIG. 7 shows corrugations defined by ridges 52 and valleys 54. The frequency or pitch of the corrugations may be varied as desired to promote any varying degree of turbulence. Therefore, more shallow corrugations as shown by ridges 52 and valleys 54 will produce less turbulence. Whereas greater corrugation pitches, as shown by ridges 56 and valleys 58, may provide increased turbulence where desired. The pitch of the corrugations and the frequency may also be varied over a single heat exchange channel to vary the heat transfer factor in different portions of the channel. The channels may contain a flat portion 60 about their periphery to facilitate closure of the channels about the sides and tops where desired.

Figure 8:
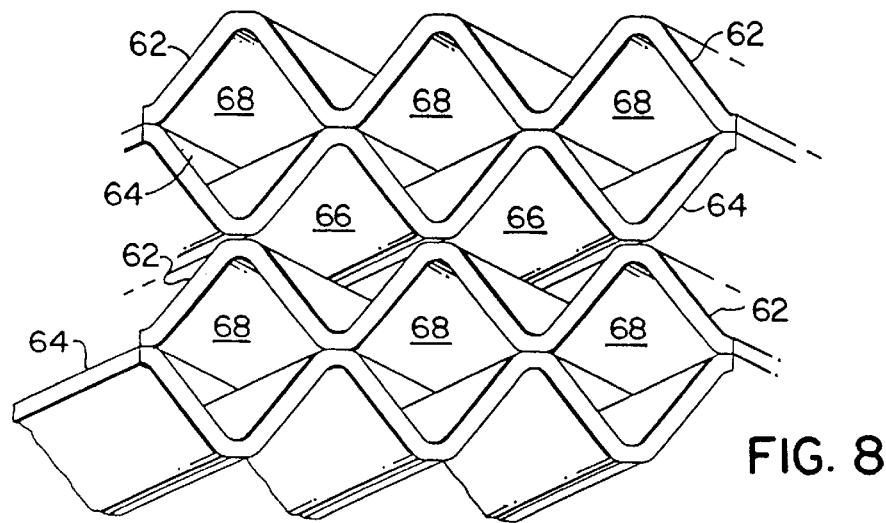
FIG. 8 is an isometric view of corrugated plates forming flow channels.

FIG. 8 shows a typical cross-section of a corrugated plate arrangement wherein the corrugations of plates 62 extend in an opposite direction to the corrugations of plates 64 thereby defining alternate reaction channels 66 and heating channels 68. FIG. 8 illustrates the preferred arrangement of corrugated plates where the herring bone pattern on the faces of opposing corrugated plates extends in opposite directions and the opposing plate faces contact each other to form the flow channels and provide structural support to the plate sections.

In general, the invention relies on relatively narrow channels to provide the efficient heat exchange across the plates. The corrugations maintain a varied channel width defined by the height of the corrugations. Ordinarily, the channel width is less than one inch on average with an average width of less than ½ inch preferred. In the case of corrugations, the average channel width is most practically defined as the volume of the channels per the cross-sectional area parallel to the primary plane of the plates. By this definition corrugations with essentially straight sloping side walls will have an average width that equals half of the maximum width across the channels.

The reaction zones for the process of this invention may indirectly contact the reactants with the heat exchange fluid in any relative direction. Thus, the flow channels and inlets and outlets of the reaction zones may be designed for cocurrent, countercurrent, or cross-flow of reactant fluid relative to the heat exchange fluid. Preferred process arrangements for practicing this invention will pass reactants in cocurrent flow or countercurrent flow to maximize contact with the heat exchange fluid for heat producing reaction zones. Cross-flow of reactants is generally preferred to minimize the pressure drop associated with the flow of reactants through the reactor. For this reason, a cross-flow arrangement can be used to provide the reactants with a shorter flow path across the reaction zone.

The shorter flow path reduces overall pressure drop of the reactants as they pass through catalyst particles retained in the reactor. Lower pressure drops can have a two-fold advantage in the processing of many reactant streams. Increased flow resistance i.e., pressure drop, can raise the overall operating pressure of a process. In many cases, product yield or selectivity is favored by lower operating pressure so that minimizing pressure drop will also provide a greater yield of desired products.

It is also not necessary to the practice of this invention that each reaction channel be alternated with a heating channel. Possible configurations of the reaction section may place two or more heating channels between each reaction channel to reduce the pressure drop on the heat exchange medium side. When used for this purpose, a plate separating adjacent heating channels may contain perforations.

Figure 10:
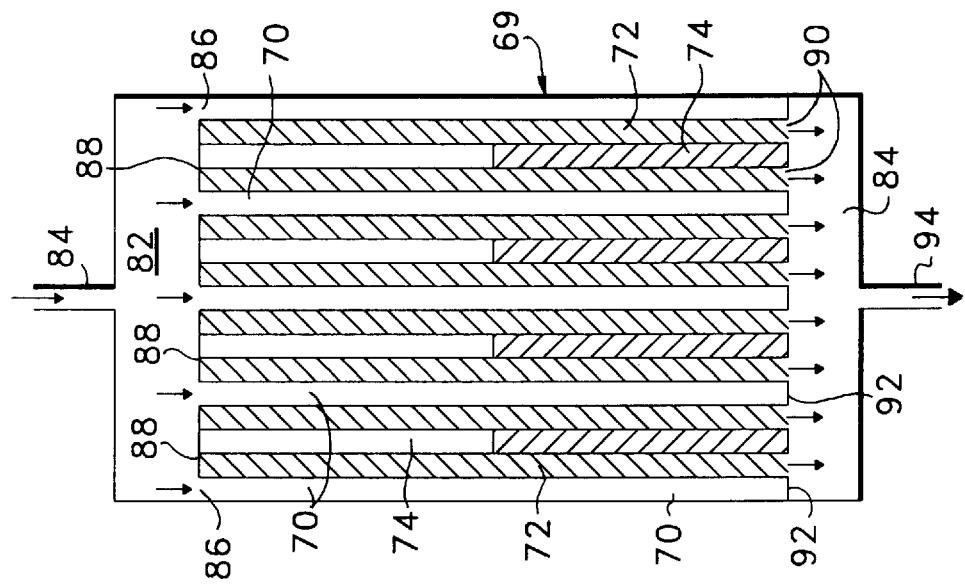
FIGS. 9 and 10 are schematic diagrams illustrating an alternate flow arrangement for reaction and heating channels in accordance with this invention.
Figure 9:
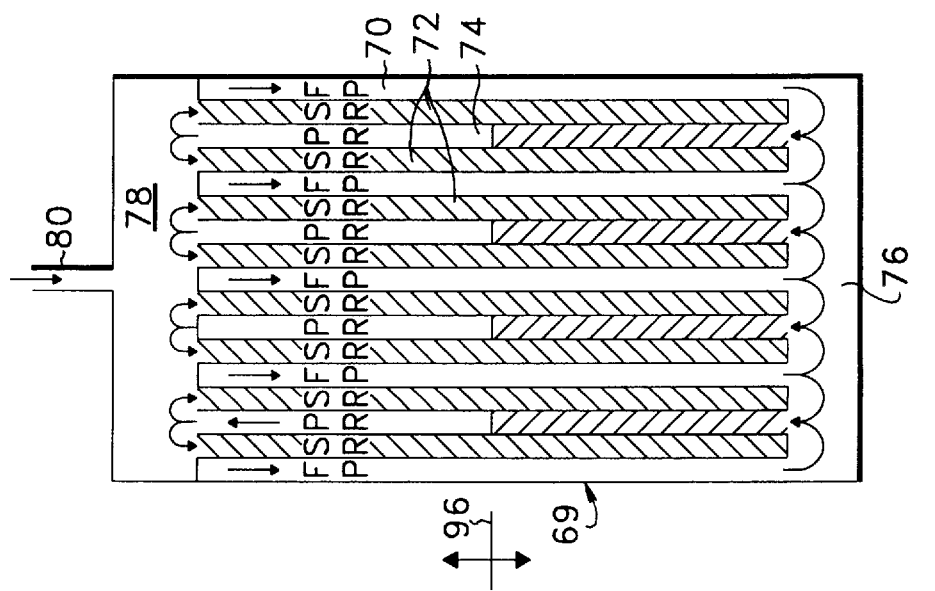

Additional channels defined by the plates can provide a variety of supplementary functions. In addition to channels for heating the feed in the preheat and catalytic sections, other channel functions may include cooling the effluent from the reaction zone and further preheating the feed against other effluent streams. A reactor arrangement 69 having multi-function channels is shown in FIGS. 9 and 10. FIG. 9 shows one such channel arrangement with the functions of the different channels coded in the schematic representation. The letters "FP" stand for a feed preheat channel. The letters "SR" indicate a secondary reaction for heating purposes and the letters "PR" represent a primary reaction.

As shown by FIG. 9, fluid flow through the channels in the desired manner requires two different collection and distribution space arrangements. Fluid flow through the distribution/collection spaces can be controlled in a manner analogous to that described and depicted by FIGS. 3–6. Looking again to FIG. 9, feed to the primary reaction zone passes through the feed preheat channels 70 where indirect heat exchange with the secondary reaction channels 72 raises the temperature of the feed to that desired for initial reaction in the primary reaction channels 74. Preheated feed from channels 70 flows into a manifold space 76. Manifold space 76 communicates the preheated feed with the primary reaction channels 74. The preheated feed passes upwardly through the primary reaction channel 74 and into another manifold space 78. Where a portion of the product is combusted as fuel, an oxygen-containing gas and optionally additional feed or combustion fuel may enter manifold space 78 through a nozzle 80. Manifold space 78 mixes any fluid entering via nozzle 80 with the primary reaction zone effluent and distributes the mixture as feed to the secondary reaction channels 72. The secondary reaction channels 72 preferably contain a combustion promoting catalyst over their entire length that promotes the exothermic secondary reaction. As the mixture passes downwardly through secondary reforming channels 72, it heats the channels 74 containing the primary reactants as well as the feed preheat channels 70.

FIG. 10 shows an additional distribution space 82 and collection space 84 that form a part of reactor 69. Partitions (not shown but similar to partitions 29 shown in FIG. 3) separate distribution space 82 and collection space 84 from space 78 and 76. Feed enters the reactor 69 via a nozzle 84. Distribution space 82 distributes the primary reforming zone to preheat channels 70 across open inlets 86. Closure plates 88 block the tops of primary reaction channels 74 and secondary reaction channels 72 where the channels are contiguous with the distribution space 82. Once distributed to the feed channels, the primary reaction feed continues to flow through the reactor 69 as described in conjunction with FIG. 9. The secondary reaction effluent leaves reactor 69 through a collection space 84 that communicates across the open bottoms 90 of secondary reaction channels 72. Outlets 90 contain an appropriate screen material to retain catalyst in the secondary reaction channels while permitting fluid to exit from the channels. The bottoms of primary reaction channels 74 are closed by closures plates 92 wherever they pass across collection space 84. A secondary reaction nozzle 94 withdraws the collected secondary reaction effluent. Any by-passing of feed between the primary and secondary reaction zones may be accomplished by external piping that communicates with any of distribution space 82, collection space 84, and manifold space 76.

Additional preheating as well as isolation of the exothermic reaction zones from direct alignment with the endothermic reaction zones is readily accomplished by varying the location of the catalyst loading between channels. The space at the one end of a channel may also be used as a feed preheating zone for the secondary reaction zone or as an effluent cooling zone. FIGS. 9 and 10 schematically illustrate a partial loading of catalyst in the channels by a catalyst level line 96. Primary reaction channels 74 may contain catalyst from below line 96 to the inlets of the channels 74. In such an arrangement, as feed flows downwardly through feed preheat channels 70, the secondary reaction zone initially heats the feed indirectly with the reaction section of the secondary reaction channels 72. The primary reaction feed, after heat exchange, enters the primary reaction channels for reaction therein. Heat from the reaction in the secondary reaction channel 72 heats the primary reaction zone in a lower portion of channel 74 as the feed passes upwardly therethrough. The effluent from the primary reaction zone continues to receive heat from the upper portion of channels 72 until it exits channels 74 and enters the tops of secondary reaction zone channels 72 for contact with the catalyst contained therein.

A variety of other combinations of channel functions can be combined in single pass or multiple pass arrangements. The use of a plate heat exchange reactor facilitates arrangement of heating channels offer many variations in desired functionality for either single or multiple stack arrangements.

For example, the upper and lower sections of channels 74, shown as theoretically separated across catalyst loading line 96, may be readily separated physically into two separate reaction zones. Collection and distribution manifolds similar to those shown in FIGS. 3–6 and 9 and 10 can be used to internally communicate fluid streams between the sections of separated channels. More usefully, the manifold arrangements may be used to externally communicate reaction channels contained in a single reaction vessel. External communication will facilitate control of gas streams to the different reaction zones and heat exchange zones. External control will also permit a wide variety of flow paths to be provided between the different channel arrangements.

Figure 11:
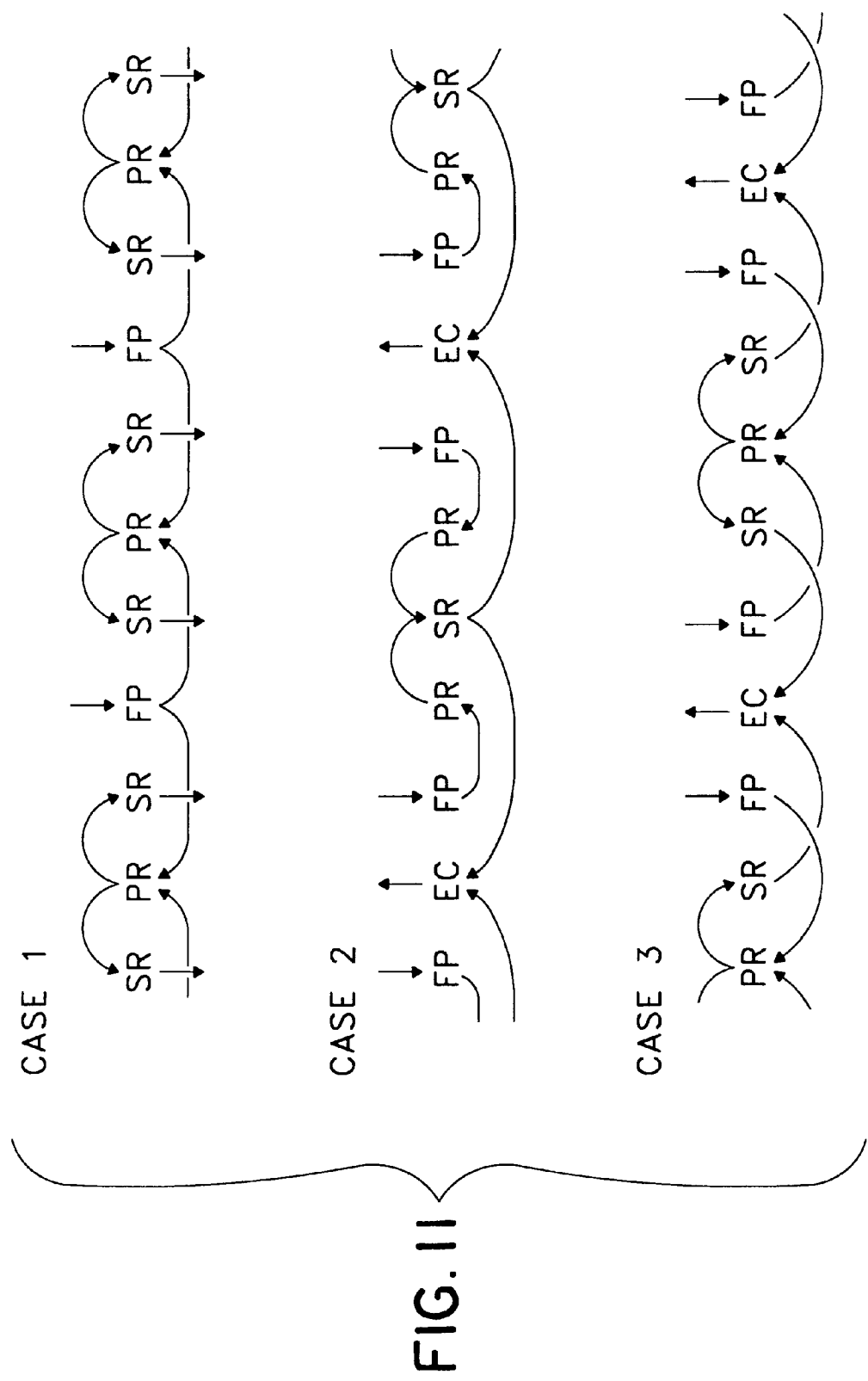
FIGS. 11 and 12 are charts showing the placement of heating and reaction zones in channels.
Figure 12:
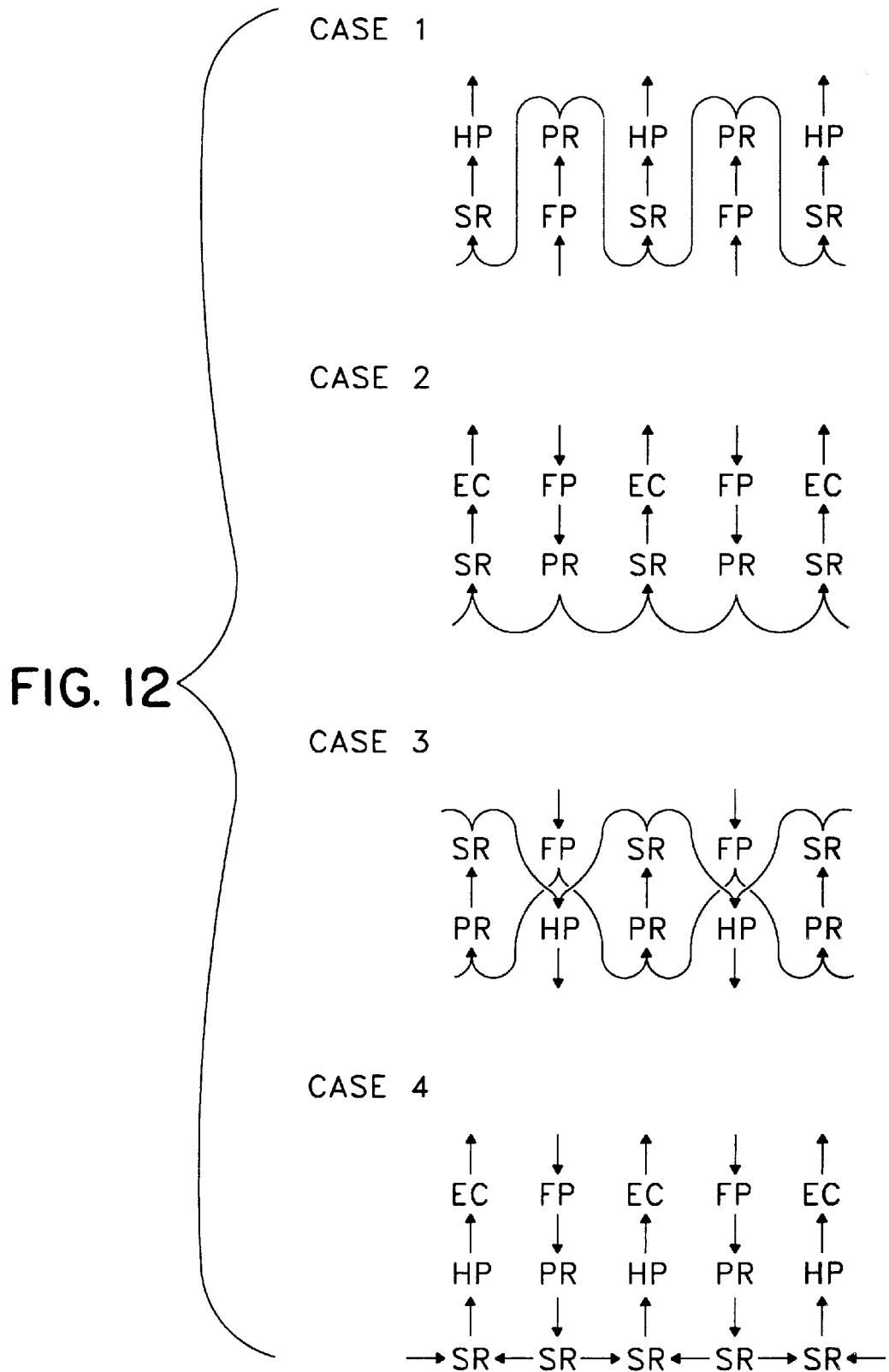

In the way of further illustration, FIGS. 11 and 12 are charts showing a coding for possible arrangements of channel functions across a plurality of channels defined by plate elements. The codes FP, SR, and PR were previously explained. Additional codes used in charts 10 and 11 include "EC" that stands for effluent cooling and "HP" that refers to a zone that contains the hot gas stream from the secondary reaction channels that heat the primary reforming reaction channels. The "HF" stands for a zone in which the feed to the primary reaction zone is further heated by indirect heat transfer against a portion of the secondary reaction channels.

FIG. 11 depicts three cases of configurations for interconnecting parallel channels in a repeating pattern of functions. Case 1 of FIG. 10 represents the arrangement of channels depicted in FIGS. 8–9 where a secondary reaction channel separates the feed preheat and primary reaction channels so that there is one primary reaction channel for every six channels overall. Case 2 represents an arrangement that cools the effluent from the secondary reaction channels against the incoming feed and provides one primary reaction channel for every 3 channels overall. Case 3 is another channel arrangement that provides one primary reaction channel and two secondary reaction channels for every 6 channels.

FIG. 12 represents further arrangements wherein multiple reaction stacks provide dual banks of channels which can be interconnected externally or internally in a manner that provides a plethora of different channel functions. All of the configurations in the chart of FIG. 12 are simplified representations of upper and lower two pass heat exchange arrangements with different functions described by the previously described codes and an additional code "HP" that represents a channel used to indirectly heat the primary reaction zone.

Case 1 of FIG. 12, shows a two pass exchanger section. In the lower channel bank the primary reaction feed undergoes indirect heat exchange with the plates that contain the secondary reforming reaction on their opposite sides. The upper channel banks react the preheated feed in the primary reaction zone opposite channels that contain the hot effluent from the secondary reaction zone and that heat the primary reaction zone. Externally connected manifolding transfers the effluent from the primary reaction zone to the secondary reforming reaction zone.

Case 2 of FIG. 12 representatively illustrates another two stack channel arrangement. The upper channel section cools the product stream from the secondary reaction zone by indirect heat exchange opposite the entering feedstream. Functionally the upper section serves essentially the same purpose as exchanger 13 in FIG. 3. The lower channel section provides indirect heating from the secondary reaction zone directly across to the primary reaction zone.

Case 3 of FIG. 12 is yet another variation on a flow scheme that uses manifolds between two banks of heating channels to establish a heat exchange arrangement similar to that shown in case 1 of FIG. 12. Case 3 differs from Case 1 by directing fluids in a countercurrent manner as opposed to the cocurrent fluid flow direction of Case 1.

Finally, case 4 shows an arrangement wherein two separate banks of heating channels are used in connection with a secondary reaction zone. The secondary reaction zone may be integral with the channels or may be located externally to the channel banks. The secondary reaction zone may also serve as a connecting manifold for communicating channels. In this arrangement the feed enters the feed preheating zone under undergoes indirect heat exchange against the effluent from the secondary reaction zone. The feed then passes from the preheating zone to the primary reaction zone. Hot gases from the secondary reaction heat the primary reaction zone by indirect heat exchange. The effluent from the primary reaction zone enters the secondary reaction zone which may be arranged as channels or as a fixed bed of secondary reaction catalyst. The effluent from the secondary reaction zone supplies hot gases to heat the primary reaction zone which then undergoes further indirect cooling with the incoming primary reaction feed.

Further enhancement of temperature control may be obtained by using intermediate injection of the oxidation fluid or additional fuel. Operating with a countercurrent or cocurrent flow of the primary reactants leaves the sides of the channels available for cross flow injection of intermediate oxidation fluid or feed. A cross flow pattern provides additional control on the generation of heat at specific locations thereby allowing adjustment of the temperature profile in the secondary reaction zone. Where the secondary reaction zone exchanges heat directly against the primary reaction zone, intermediate injection can also be used to influence the temperature profile within the primary reaction zone.

EXAMPLE

The effect of using the process and channel arrangements of this invention to maintain isothermal conditions was investigated in a hydrocarbon conversion process for the dehydrogenation of paraffins. A simulation based on the ability of this invention to maintain isothermal conditions was prepared based on a feedstream having a composition given in Table 1. The isothermal conditions that resulted from this invention were simulated in a dehydrogenation process using a channel configuration as schematically depicted in FIG. 2 wherein methane was independently combusted to provide the heat input to the process.

In this process simulation, a feedstream carried via line 10 and having the composition given in Table 1 passes into a heat exchanger 12 that raises the feedstream temperature from approximately 370° C. to 390° C. At the same time, the dehydrogenation zone effluent having the relative composition given for stream 14 is withdrawn from exchanger 12 via line 24.

Line 18' carries the partially heated feedstream into preheat zone 40 that receives heat from heating zone 28'. Indirect heat exchange across a series of heat transfer plates raises the temperature of the feed to about 480° C. as it exits preheat zone 40. The process simulation of preheat and catalytic reaction zone portions is based on the use of a plate heat exchange bundle having 250 layers of catalyst, a preheat zone length of about 1.1 m and a catalytic zone length of about 0.37 m. The plates define the reaction channels which alternate between the heating channels and have a thickness of about 1.2 mm, corrugations with a depth of about 10 mm and a width of about 5500 mm. The plates are placed next to each other in an alternating pattern of corrugations, such that the peaks of the corrugations are in contact. The reaction channels and heat exchange channels operate at an average pressure of about 20 psig.

The heated feedstream undergoes dehydrogenation to produce the product stream having the previously described composition for line 14. Continued indirect heating from the heating zone 28' maintains the temperature of the product stream from catalytic zone 42 at an outlet temperature of 474° C. The catalytic reaction section contains a typical dehydrogenation catalyst comprising platinum on an alumina support.

Line 30 delivers a mixture of methane, oxygen, and carbon oxides to the heating zone 28' to supply the indirect heat input for preheat zone and catalytic zone. Approximately 74,000 kg moles/hr of the circulating heating mixture is purged from the outlet line 32 via line 38 while the remainder of the heating mixture along with 7,000 kg moles/hr of methane and an air stream, supplying 14,000 kg moles/hr of oxygen, return to the input line 30.

TABLE

| Stream Description kg mole/hr | 10 | 14 |
|---|---|---|
| $H_2O$ | 13.3 | 13.3 |
| Hydrogen | 2733.4 | 2824.0 |
| Methane | 57.9 | 57.9 |
| Ethane | 150.3 | 150.3 |
| Propane | 54.4 | 54.4 |
| n-Butane | 34.8 | 34.8 |
| n-Pentane | 20.2 | 20.2 |
| $n-C_6-C_9$ | 12.1 | 11.9 |
| $n-C_{10}$ | 139.0 | 116.1 |
| $n-C_{11}$ | 168.8 | 136.7 |
| $n-C_{12}$ | 116.9 | 91.9 |
| $n-C_{13}$ | 39.8 | 30.2 |
| $n-C_{14}$ | 2.8 | 2.0 |
| 1-Nonene | — | .2 |
| 1-Decene | .8 | 23.7 |
| 1-Undecene | .3 | 32.4 |
| 1-Dodecene | .1 | 25.1 |
| 1-Tridecene | — | 9.6 |
| 1-Tetra decene | — | .7 |
| Total: | 3544.9 | 3634.7 |

What is claimed is:

1. A process for contacting reactants with a catalyst in a reaction zone and indirectly heating the reactants by contact with a heating medium, the process comprising:

a) passing a reactant stream through a plurality of narrow reaction channels defined by principal spaced apart plates and heating the reactant stream in the absence of catalyst in a first portion of the narrow reaction channels;

b) passing a heating medium through a plurality of narrow heating channels defined by the principal plates and indirectly heating the reactant stream in the first portion of the reaction channels across the plates with the heating medium in a preheat portion of the heating channels to provide a heated reactant stream in the reaction channels;

c) passing the heated reactant stream through a second portion of the reaction channels and contacting the heated reactant stream with a catalyst in the second portion of the reaction channels to produce a reacted stream; and, d) indirectly heating the second portion of the reaction channels with heating medium as it passes through a primary heating portion of the heating channels.

2. The process of claim 1 wherein the heating channels contain an oxidation catalyst.

3. The process of claim 1 wherein the principal plates define alternate reaction channels and heating channels.

4. The process of claim 2 wherein the heating medium comprises methane and oxygen and the combustion of methane provides at least a portion of the heat for the reaction channels.

5. The process of claim 1 wherein the first and second portions of the reaction channels and the preheat and heating portions of the heating channels are continuous.

6. The process of claim 1 wherein the plates define corrugation and the corrugations maintain the spacing of the plates.

7. The process of claim 1 wherein the catalyst in the reaction channels comprises a particulate material retained in the channels.

8. The process of claim 1 wherein the reaction channels have an average width of less than 1 inch.

9. A process for contacting reactants with a catalyst in a reaction zone while indirectly preheating and heating the reactants by contact with combustion gases formed in a heat producing zone, said process comprising:

a) passing a reactant stream through a plurality of narrow reaction channels defined by principal spaced apart plates b) heating the reactant stream in a first portion of the channels in the absence of catalyst to produce a heated reactant stream;

c) passing the heated reactant stream to a second portion of the channels and reacting the heated reaction stream by contact with a heterogeneous catalyst;

d) passing a methane-containing stream to a plurality of narrow heating channels defined by the principal spaced apart plates and combusting the methane-containing stream by contact with a combustion catalyst to indirectly heat the first and second portion of the heat reaction channels.

10. The process of claim 9 wherein the plates define alternate reaction channels and heating channels.

11. The process of claim 9 wherein the plates define corrugation and the corrugations maintain the spacing of the plates.

12. The process of claim 9 wherein the combustion catalyst comprises a particulate material retained in the heating channels.

13. The process of claim 9 wherein the reaction channels have an average width of less than 1 inch.

14. An apparatus for contacting reactants with a catalyst in a reaction zone while indirectly heating the reactants by contact with combustion gases formed in a heat producing zone, the apparatus comprising:

a plurality of alternate reaction channels and heating channels defined by a plurality of primary plates to have a reactant inlet at one end of the reaction channels, a reactant outlet at an opposite end of the reaction channels, a heating fluid inlet at one end of the heating channels and a heating fluid outlet at the opposite end of the heating channels;

means for excluding a solid catalyst from a preheat portion of the reaction channels located downstream of the reactant inlet and retaining a solid catalyst in a catalytic portion of the reaction channels located downstream of the preheat portion; and wherein the heating channels define a combustion zone and the heating channels retain a combustion promoting catalyst.

15. The apparatus of claim 14 wherein the apparatus includes means for delivering a reactant stream to the reactant inlet and for withdrawing a reacted stream from the reactant outlet and means for delivering a heating fluid to the heating fluid inlet and for withdrawing a heating fluid from the heating fluid outlet.

16. The apparatus of claim 14 wherein the combustion-promoting catalyst comprises an oxidation catalyst and wherein the apparatus further comprises an oxygen conduit for supplying oxygen to the heating channels.

17. The apparatus of claim 14 wherein the plates are flat.

18. The apparatus of claim 14 wherein the plates define corrugations and the corrugations maintain the spacing of the plates.

* * * * *